United States Patent [19]

Diamond et al.

[11] Patent Number: 4,629,689

[45] Date of Patent: Dec. 16, 1986

[54] BINDING ASSAY WITH AMPLIFIED READ-OUT AND GAS-PHASE DETECTION

[75] Inventors: Steven E. Diamond, Springfield, N.J.; Francis J. Regina, Brooklyn, N.Y.

[73] Assignee: Allied Corporation, Morris Township, Morris County, N.J.

[21] Appl. No.: 645,202

[22] Filed: Aug. 29, 1984

[51] Int. Cl.[4] .................. G01N 33/53; G01N 33/542
[52] U.S. Cl. .......................................... 435/7; 435/6;
  435/14; 435/18; 435/803; 435/807; 435/810;
  436/63; 436/94; 436/501; 436/537; 436/541;
  436/825; 436/808; 935/78
[58] Field of Search ................. 435/6, 7, 14, 18, 803,
  435/807, 810; 436/63, 94, 501, 537, 541, 825,
  808; 935/78

[56] References Cited

U.S. PATENT DOCUMENTS 4,197,369 4/1980 Weaver ............................ 435/18
4,322,495 3/1982 Kato .................................. 435/810

FOREIGN PATENT DOCUMENTS 2078370 1/1982 United Kingdom ................ 435/7
2102946 2/1983 United Kingdom ................ 435/7

OTHER PUBLICATIONS

Vela, Clinical Chemistry, 14(8), pp. 837–838, (1968).
Hrivnak–Chemical Abstracts 72:28200A (1970).
Matsunaga–Chemical Abstracts 92:140189T (1980).

Primary Examiner—Christine M. Nucker
Assistant Examiner—Robert Benson
Attorney, Agent, or Firm—Alan M. Doernberg; Gale F. Matthews

[57] ABSTRACT

At the conclusion of a selective binding assay (e.g., immunological or nucleic acid), an enzyme is present in modulated concentration and/or activity to moderate a chemical reaction such as the cleavage of o-nitrophenyl-$\beta$-D-galactopyranoside. After a controlled period, the enzymatic product is transferred to the gas phase and concentrated relative to other components in the enzymatic reaction mixture, such as by extraction into ethyl ether, injection into a gas chromatography column and detection by flame ionization or electron capture. Kits for such assays are also disclosed.

30 Claims, 10 Drawing Figures

BINDING ASSAY WITH AMPLIFIED READ-OUT AND GAS-PHASE DETECTION

BACKGROUND OF THE INVENTION

The present invention relates to methods for the determination of a target binding pair member, such as an antigen, antibody, hapten or nucleic acid strand in a biological sample; and the invention also relates to reagents or kits used for such determination method. The method involves, in general, amplified read-outs, such as by the use of enzymes, and also involves transferring a detectable moiety into a gas phase where the detectable moiety is detected (determined either quantitatively or qualitatively).

Enzyme immunoassays are well known in which a binding reaction, such as between sample and labeled antigens and reagent antibodies, are conducted. At the conclusion of the assay, with or without a separation, an enzyme is present in a phase, either a liquid phase or a solid phase, and the concentration and/or activity of the enzyme is functionally related to the concentration (or presence) of the target binding pair member in the sample assay. Exemplary references to such enzyme immunoassays include Enzyme-Immunoassay (CRC Press 1980, E.T. Maggio ed.). Such enzyme immunoassays can generally be characterized as either heterogeneous (competitive or non-competitive) or homogeneous. These different geometries lead to different results in that, in the competitive-heterogeneous assay, higher sample concentrations of the target antigen generally lead to lower concentrations of enzyme in the solid phase after separation. In the heterogeneous non-competitive assay (e.g., a sandwich assay) higher concentrations of the target antigen or antibody generally lead to higher concentrations (and therefore activities) of enzyme on the solid phase after separation. In the homogeneous assay, the concentration of enzyme in the liquid phase after the binding reaction is unaffected; however, the activity of the enzyme is modulated by the target concentration, with some forms having lower enzyme activity with higher target antibody concentrations, but other forms having higher enzyme activities with higher target antigen concentrations. Surveys of geometries for enzyme immunoassays are contained in E.T. Maggio, Enzyme-Immunoassay (CRC Press, Inc., Boca Raton, FL 1980); T. T. Ngo et al., Mol. & Cellular Biochem., Vol. 44, pp. 3-12 (1982); C. Blake et al., Analyst, Vol. 109, pp. 533-547 (May 1984).

Assays for target polynucleotide sequences (DNA or RNA) have been described based upon the specific hydrogen bonding between purine/pyrimidine nucleotides. The most common form of these assays involves immobilizing the nucleic acid of a sample in single stranded form on a support. Thereafter a probe, containing nucleotide sequences complementary to the target strand, is applied with a label such as either an enzyme or a binding member (e.g., biotin or an antigen) pendent to the probe polynucleotide. If the enzyme is not directly attached to the probe polynucleotide, it may be indirectly attached by using a probe bearing an antigen (e.g., biotin) and subsequently contacting the support with an enzyme linked to an antibody (or, similarly, avidin or strepavidin, each of which binds to biotin). After washing the coated support to remove any unbound probebiotin conjugate or any unbound avidin-enzyme conjugate, the coated support is contacted with substrates for the enzymatic reaction. After a controlled period, either reactants or products of the enzymatic reaction may be assayed, with increased amounts of enzymatic reaction corresponding to increased concentrations of the target polynucleotide in the sample. Such methods are described generally in Falkow et al., U.S. Pat. No. 4,358,535 (1982); EPO 70,687 of Heller et al. (Standard Oil 1983) (page 6), and forms of such methods employing biotin or the like attached to the probe are described in EPO No. 63,879 of Ward et al. (Yale University 1982); EPO No. 97,373 of Rabbani et al. (Enzo Biochem, Inc. 1984); Leary et al., Proc. Nat. Acad. Sci., Vol. 80, pp. 4045–4049 (1983).

A second type of polynucleotide assay which has been described is the "sandwich" assay, somewhat similar to sandwich assays used for immunochemical analyses. In such sandwich assay two probe polynucleotides are used, each complementary to a portion of the target polynucleotide strand. The first probe polynucleotide is attached to a support. The second probe polynucleotide can be attached to either an enzyme or to biotin (which is subsequently attached to the enzyme using an avidinenzyme conjugate or the like). By simultaneous or sequential incubation, a complex is formed containing support linked by the first probe target polynucleotide strand, and the second probe (and, optionally, further through biotin and avidin) to the enzyme. After appropriate washing, such complexes should represent the only enzyme remaining coated on the support. By then introducing the reactants of the enzymatic reaction, and assaying for the products of the enzymatic reaction, enzyme concentration on the first phase (the support) can be quantified. Such enzymatic activity should be positively related to the concentration of the target nucleotide strand in the sample. See EPO No. 70,687 (Standard Oil 1983) (pages 8–10); PCT Application WO 83/01459 of Orion-Yhtma Oy (Apr. 29, 1983).

A third general type of polynucleotide assay has been described in U.S. patent application Ser. No. 607,885 of Diamond et al., entitled "Displacement Polynucleotide Assay And Method Polynucleotide Complex Reagent Therefor", assigned to Allied Corporation and Genetics Institute Inc. and filed on May 7, 1984. By virtue of the assignment of the present application to Allied Corporation, it is believed that there is sufficient common assignment of these two applications for this reference. In such systems, the probe polynucleotide, complementary to the target polynucleotide, is provided in solution or on a support, but paired through hydrogen bonding to a second polynucleotide, called the labeled polynucleotide. In some forms of that invention, the labeled polynucleotide contains either an enzyme as a label, or contains a binding determinant such as biotin as the label. In either case, when this reagent complex is contacted with sample, target polynucleotides in the sample will displace labeled polynucleotide from the reagent complex. By either conducting a separation or by the effect of the displacement on the activity of the enzyme (frequently due to steric factors) the activity and/or concentration of the enzyme in a phase (generally a liquid phase) will be positively related to the concentration of target polynucleotide in the sample.

While all of the above procedures take advantage of the amplification of an enzyme to enhance the detectable moieties compared to the target binding pair member moieties, a common problem in such assays is distinguishing such detectable moieties from the many other organic and biological materials present in the phase, particularly liquid phase, wherein the binding reaction and/or the enzymatic reaction are conducted. In the case, particularly, of fluorescence or absorption measurements, such interferences are quite common and can lead to significantly less selectivity and/or sensitivity to the assay than is dictated by the specific binding reaction or the enzymatic reaction. Nevertheless, any method proposed to overcome these interferences must offer simplicity and speed similar to that of the first two reactions in order not to unduly complicate or delay the obtainment of qualitative or quantitative results from the assay.

BRIEF DESCRIPTION OF THE INVENTION

The present invention combines the amplification effects of specific binding reactions coupled with enzymatic (or other moderated) reactions with the high sensitivity and low background attainable with gas-phase sensing of detectable moieties. In particular, the present invention includes a method for the determination of a target binding pair member in a biological sample comprising the steps:

(a) performing a specific binding reaction for the target binding pair member;

(b) providing a reaction moderating moiety in a first phase, the concentration or activity of the reaction moderating moiety being a function of the amount of target binding pair member participating in the specific binding reaction;

(c) providing in contact with the first phase, a precursor convertible by chemical reaction moderated by the reaction moderating moiety into a detectable moiety in a volatile form;

(d) transferring into a gaseous phase detectable moiety formed from the precursor;

(e) concentrating detectable moiety relative to other components of the first phase; and (f) detecting the detectable moiety which has been concentrated and transferred into the gaseous phase.

The present invention also includes a novel kit for the determination of a target binding pair member in a biological sample comprising:

(a) a first reagent comprising an enzyme conjugated to a specific binding pair member capable of competing with the target binding pair member in a specific binding reaction, (b) a non-volatile conjugate containing a linkage cleavable by chemical reaction moderated by the enzyme and containing a detectable moiety released in a volatile form from the conjugate upon cleavage of the linkage by the enzyme, (c) means for concentrating and transferring the detectable moiety to a gas phase, and (d) means for detecting moiety which has been concentrated and transferred to the gas phase.

BRIEF DESCRIPTION OF THE DRAWINGS

FIGS. 1A-1K illustrate the various embodiments of the described immunoassays.

DETAILED DESCRIPTION OF THE INVENTION

The present invention will be described first in terms of the present method, then in terms of the reagents used for the method and finally in terms of exemplary target binding pair members for the method. In many instances targets which are antigens, antibodies, haptens or polynucleotides will be discussed for illustrative purposes, it being understood that each of these and other specific target binding pair members can be assayed for in the present invention, with certain forms being preferred for certain target binding pair members. In discussing the method, geometries for the specific binding reaction (Step a) and the reaction moderating step (Step b) will be discussed first; next the enzymatic reaction (Step c) will be discussed; and finally the steps of transferring the detectable moiety (Step d) and detecting the detectable moiety (Step e) will be discussed.

Figure 1A:
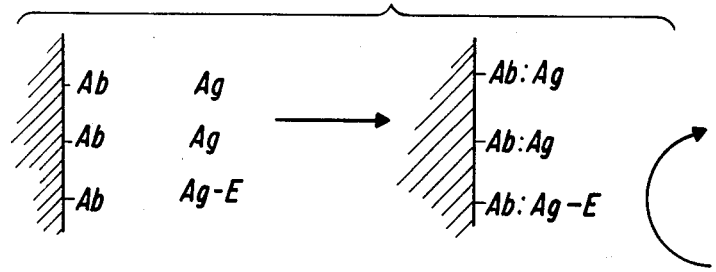

The geometries for steps a and b of the present invention can be any of those described in the above references for either enzyme immunoassays or polynucleotide assays. Nine such exemplary geometries are illustrated in FIGS. 1A-1K of the attached figures, to which reference is made herein. In FIG. 1A, the antigen (Ag) which is the target of the assay (and is contained in varying amounts if at all in a sample) is contacted simultaneously with an antibody (Ab) attached to a support(s) such as a test tube wall or polystyrene beads and an antigen-enzyme conjugate (Ag-E). Because of the specific binding of the antibody (Ab) to both the target antigen (Ag) and the antigen of the antigenenzyme conjugate (Ag-E), a competition will occur wherein some of the immobilized antibody will be bound with target antigen and others will be antigen-enzyme conjugate. Provided that the antibody is present in amounts less than that required to bind all of the antigen-enzyme conjugate, the amount of antigen-enzyme conjugate bound to the solid support will decline as the amount of target antigen increases. After this competitive binding step, the coated substrate is washed and reactants for the enzymatic reaction are added. In the present invention, this reaction (indicated in FIG. 1A by a curved arrow) involves a cleavage of a conjugate or other chemical reaction forming a volatile moiety. In this respect it differs from the enzymatic reactions commonly used which yield a fluorescent, absorbant, luminescent or otherwise chemically or physically reactive moiety. Nonetheless, as in the conventional immunoassays, the amount of reaction products formed after a fixed period of enzymatic reaction is positively related to the enzyme concentration on the support after the separation. Since this enzyme concentration is negatively related to the antigen concentration in the sample, the concentration or amount of enzymatic reaction products will also be negatively related to the target antigen concentration or amount.

Figure 1B:
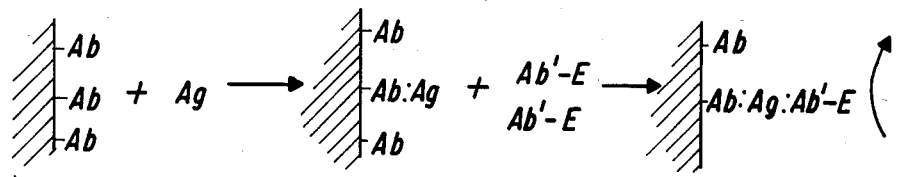

FIG. 1B illustrates a second form of enzyme immunoassay, commonly referred to as a sandwich enzyme immunoassay. In this geometry, an antibody (Ab) reactive against the target antigen (Ag) is immobilized on a support. When the sample is introduced, any target antigen (Ag) in the sample will bind to the supported antibody. By then adding a reagent in which enzyme is coupled to a material reactive against antigen/antibody complexes (for example, a second antibody Ab') complexes are formed wherein the enzyme is linked to the support via the antigen (Ag), antibody (Ab) and second antibody (Ab') as illustrated in FIG. 1B. The higher the amount or concentration of target antigen (Ag), the more such complexes are formed (it being understood that the supported antibody (Ab) and second antibody-enzyme conjugate (Ab'-E) are provided in amounts sufficiently high not to become the limiting reagent). Such antibody-enzyme conjugate (Ab'-E) will not react with antibody (Ab) that is supported to which antigen (Ag) has not bound. After washing off unreacted second antibody-enzyme enzyme conjugate (Ab'-E), the enzymatic reactants or substrates are then added. Again, after a fixed period, enzymatic reaction products are assayed: in the present invention after transfer to the gas phase and concentration as described below, but in conventional assays by measuring absorbance, fluorescence, luminescence or other properties in a liquid phase. In this geometry, the enzyme concentration on the support after binding and separation is positively related to antigen (Ag) concentration in the sample. Accordingly, concentration of enzymatic reaction products in the fixed period is also positively related to the target antigen (Ag) concentration.

Figure 1C:
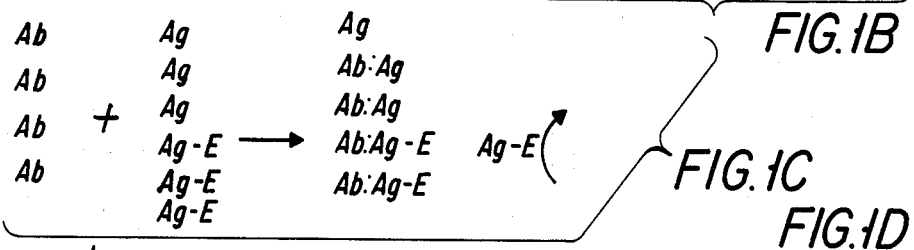

FIG. 1C illustrates a homogeneous immunoassay of the general type currently used, but in a form useful in the present invention as described below. In this geometry, the sample, potentially containing various amounts of the target antigen (Ag), is mixed both with an antigen-enzyme conjugate (Ag-E) and with a fixed and limiting amount of antibody (Ab). In the competitive binding reaction that occurs, some antigen-enzyme (Ag-E) remains unbound, some antigen-enzyme (Ag-E) becomes bound to antibody (Ab) (as Ab:Ag-E) (with steric factors of such binding reducing or eliminating the enzymatic activity) and some of the target antigen (Ag) also becomes bound to antibody (Ab) (as Ab:Ag). As in the first geometry described in reference to FIG. 1A, the greater the amount of target antigen (Ag), the more of the antibody sites are taken by a target antigen (Ag), and therefore the more of the antigen-enzyme conjugates (Ag-E) are left uncoupled or unreacted by antibody. By then adding the reagents for the enzymatic reaction and monitoring over a fixed period, the enzymatic activity can be assayed. Enzymatic reaction products are present in in increased amounts over the fixed period when increased amounts of target antigen (Ag) are present in the sample. In the present invention, as described below, such enzymatic reaction products are detected after concentration and transferring to the gas phase.

Figure 1D:
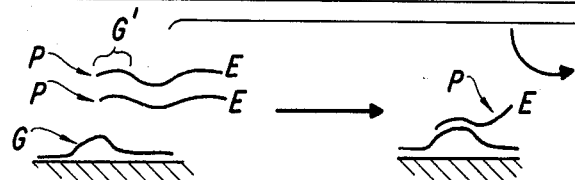
Figure 1D:
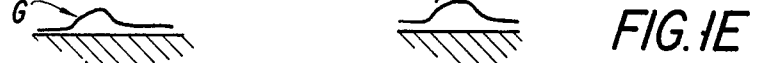
Figure 1E:
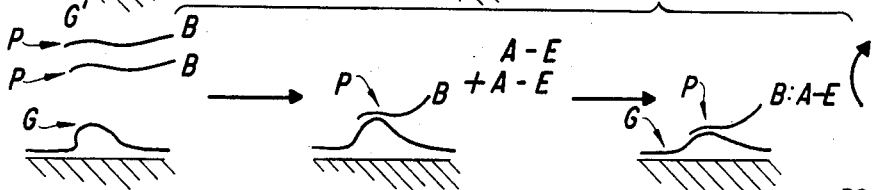

FIG. 1D illustrates a first form of nucleic acid assay geometry useful in the present invention. In this geometry, the sample nucleic acid (containing target sequence G) is immobilized in single-stranded form on a solid phase such as nitrocellulose filter paper. That coated paper is then contacted with a complex of a probe polynucleotide (P) containing polynucleotide sequences (G') complementary to the target nucleotide sequences (G) in the target of the sample. In addition, probe polynucleotide (P) is covalently bonded to an enzyme (E). After suitable incubation periods and separations (especially washing) the coated paper is then contacted with the enzymatic reactants. By assaying for enzymatic reaction products (after transfer to the gas phase and concentration in the present invention) a quantitative measurement may be obtained which is functionally and positively related to the target polynucleotide sequence (G) amount or concentration in the sample. A modification of this procedure is illustrated in FIG. 1E in which the sample immobilized on filter paper is contacted first with probe polynucleotide (P) linked to biotin (B) and then with avidin or strepavidin (A) linked to the enzyme (E). After sufficient washing and other separation, the coated filter paper is now contacted with enzymatic reactants. To the extent that enzyme (E) is coated on the paper (preferably only by specific attachment as shown via sample (G), probe (P), biotin (B) and avidin (A), but in many cases frequently also by non-specific binding), enzymatic products will accumulate over a fixed period of time. Again, the concentration of enzymatic reaction product (detected in the present invention after transfer to a gas phase and concentration) will be a function of and positively related to the amount or concentration of the target polynucleotide sequence (G) in the sample.

Figure 1F:
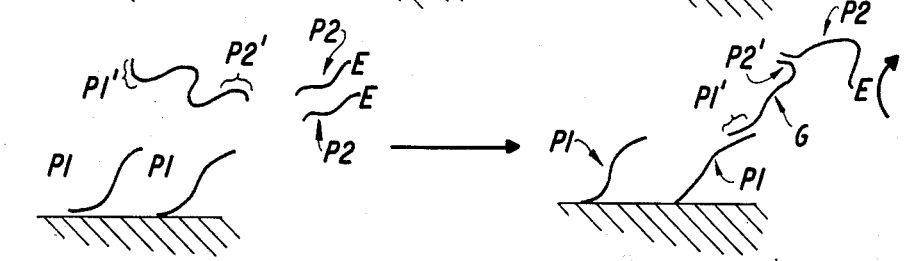

FIG. 1F illustrates a sandwich polynucleotide assay. In this case, the support or solid phase (e.g., filter paper) has bound to it a first probe (P1) containing nucleotide sequences complementary to a first nucleotide sequence of the target polynucleotide. A second probe (P2) is covalently linked to an enzyme (E) [or possibly to biotin or the like and avidin-enzyme conjugate (A-E) is added later] and the two probes (one on the solid phase, the other in the solution) are incubated with the sample. Target polynucleotide sequences in the sample will link both to P1 and to P2 causing the formation of a complex in which the enzyme is linked to the solid phase either, as shown, via P1, target polynucleotide (G) and P2 or, (as described above but not illustrated) via P1, sample (G), P2, biotin and avidin. After washing to remove unbound enzyme and the like, enzymatic reactants are now added and enzymatic reaction products are assayed (in the present invention after transference to the gas phase and concentrating). The amount of such enzymatic reaction products after a fixed period of enzymatic reaction is a function of, and positively related to, the concentration or amount of target polynucleotide present in single stranded form in the sample.

Figure 1G:
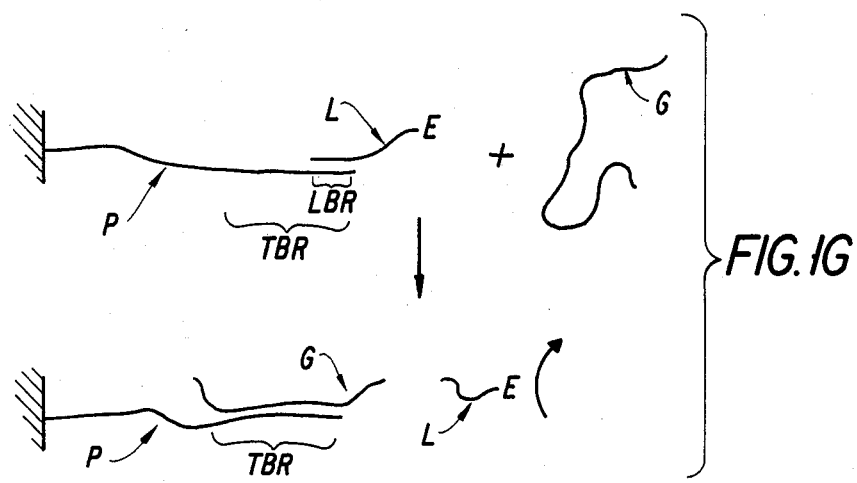

FIG. 1G illustrates a first or heterogeneous form of the displacement polynucleotide assay described in the application of Diamond et al. U.S. Ser. No. 607,885. In this assay, a substrate such as polystyrene beads is provided linked by absorption or, preferably, by covalent bonds to the probe polynucleotide (P). Also provided in the reagent complex is a labeled polynucleotide (L) to which, in this form, the enzyme (E) is attached. The labeled polynucleotide is bound via purine, pyrimidine base pairing to a portion (LBR) of the target binding region (TBR) of the probe polynucleotide (P) to which the sample can ultimately bind (the geometry and size of these regions is described in more detail in application Ser. No. 607,885, disclosure of which is incorporated herein by reference). When this immobilized reagent complex is contacted with sample, target polynucleotide sequences in the sample will bind to the probe polynucleotide and displace the labeled polynucleotide from the solid phase. The liquid phase may be separated from the solid phase and enzymatic activity determined therein; or, alternatively, the enzyme may be permitted to migrate to a different place in the reaction mixture, remote from the reagent complexes, where it can contact enzymatic reactants. In either case, by permitting the enzymatic reaction to occur for a known period, enzymatic reaction products (transferred in the present invention to the gas phase and concentrated) can be detected and quantitated. Such enzymatic reaction products will be a function of and positively related to the amount of enzyme linked to labeled polynucleotide (L) that are displaced from the solid phase and therefore also positively related to target polynucleotide (G) amount or concentration in the sample.

Figure 1J:
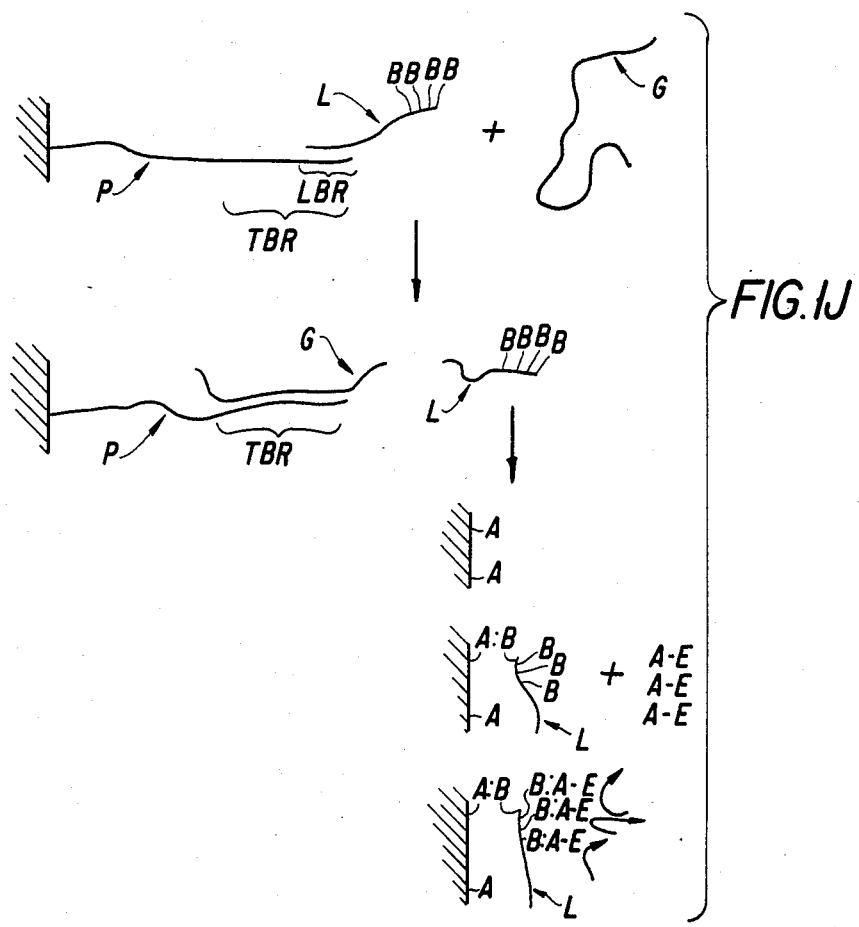

A second form of heterogeneous displacement polynucleotide assay, of the type described in Diamond et al. U.S. application Ser. No. 607,885, is illustrated in FIG. 1J. In this case, the labeled polynucleotide (L) bound via purine/pyrimidine base pairing to the immobilized probe polynucleotide (P) contains a multiplicity of pendant biotin moieties (B). Reaction with the sample will cause displacement of such labeled polynucleotides in an amount functional of and positively related to the concentration or amount of target polynucleotide sequences (G) in the sample. Such labeled polynucleotides (L) in the liquid phase can then be passed through or in contact with avidin or strepavidin molecules (A) attached to a different solid phase (e.g., a strepavidin column). Because of the strong binding of biotin (B) to either avidin or strepavidin (A), such labeled polynucleotides (L) will adhere through at least some of the pendant biotin moities (B). Because, however, of steric factors, it is believed that many of the pendant biotin moieties (B) will not be able to adhere to avidin molecules (A) (especially if the avidin molecules are spread from each other by distances greater than the length of the labeled polynucleotide L). Such other biotin moieties will be pendant and will selectively bind to avidin-enzyme complexes (A-E) then passed through the column. By then washing and testing the solid phase for enzyme (E) linked to the solid via avidin (A), biotin (B), and labeled polynucleotide (L), biotin (B) and column avidin (A), enzymatic activity can be determined in the usual way (addition of enzymatic reactants, transfer of direct or indirect enzymatic products to the gas phase and concentration). Determination of such enzymatic products will give a value positively related to the pendant biotin moieties, and thus to the labeled polynucleotide (L) displaced, and finally to the target polynucleotide (G) in the sample.

Figure 1K:
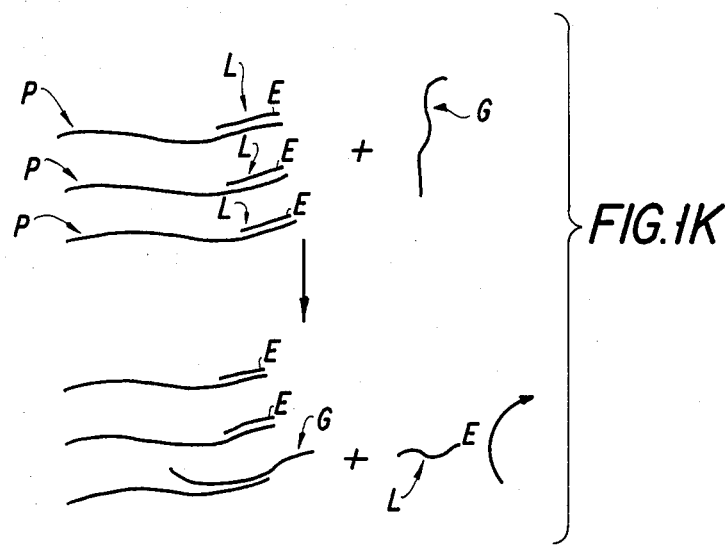

A homogeneous displacement polynucleotide assay geometry useful in the present invention is illustrated in FIG. 1K. In this case, the probe polynucleotide (P), containing a target binding region complementary to the target polynucleotide (G) is provided with a labeled polynucleotide (L) containing enzyme (E) (shown as directly linked, but potentially linked indirectly by avidin-biotin or by the like) all in solution. In this reagent complex, the enzyme (E) should be held by the base pair binding in close proximity either to the probe polynucleotide (P) itself or to some large sterically hindering moiety attached to the probe polynucleotide (P). By contacting then with the sample, some labeled polynucleotide (L) (with pendant enzyme) will be displaced from the reagent complex. By then adding enzymatic reactants, an enzymatic reaction will occur in large part only where enzyme (E) has been displaced, and to a great extent not where the enzyme (E) is still sterically hindered in the reagent complex. By detection of enzymatic products (after transference to the gaseous phase and concentration in the present invention), a value can be obtained which is a function of and positively related to labeled polynucleotides displaced from the reagent complex and thus also positively related to target polynucleotides (G) in the sample.

In view of the preceeding nine exemplary discussions, it should be apparent that a wide variety of specific binding reactions are possible wherein the concentration or activity of an enzyme linked to a binding pair member can be affected either positively or negatively by the concentration or amount of target binding pair member in a sample. While the above illustrations speak only to target antigens, and target polynucleotide sequences, it should be readily apparent that various of these geometries will apply to target haptens, target antibodies, target hormones and target receptors (such as are produced by T-cells). The amplification effect of the enzyme (or other moderating moieties such as catalysts and cofactors) is helpful in improving the sensitivity of all of the above assays. It is especially helpful, however, where the target binding member is present in a low copy number. Such is frequently the case with viral and bacterial antigens, DNA and RNA.

Once both the specific binding reaction or reactions and the enzymatic reaction are completed, a detectable moiety is transferred in the present invention to a gaseous phase. In some preferred forms, the substrate for the enzymatic reaction is selected as one in which the enzymatic reactant is either nonvolatile or relatively nonvolatile, but at least one of the enzymatic reaction products is volatile or relatively volatile. In the preferred forms of the invention, the enzymatic reactant is a conjugate and the enzyme is a hydrolytic enzyme. In such cases the conjugate is essentially or relatively nonvolatile, but a detectable moiety is present in the conjugate linked by an enzymatically-cleavable linking moiety to the remainder of the conjugate. Such detectable moiety should both be volatile or relatively volatile (as described in more detail below) and detectable by the detection means chosen (as also described in more detail below).

In the course of performing the process of the present invention, this detectable moiety should be transferred into a gaseous phase. It is contemplated that such transference can take the simple form of evaporating the detectable moiety from an aqueous liquid phase in which the conjugate has been cleaved (i.e., the aqueous enzymatic reaction mixture). It is also contemplated that the detectable moiety can be evaporated from some different aqueous phase, or from some modified form of the aqueous phase after various physical or chemical treatments or separations following the enzymatic reaction. It is further contemplated, however, that the detectable moiety may be extracted from the aqueous phase into an organic liquid phase and then evaporated from the organic liquid phase. In such instances, non-toxic but water immiscible organic solvents such as ethers, ketones, esters, aliphatic hydrocarbons and aromatic hydrocarbons are preferably used to extract the detectable moieties and relatively few other low polarity materials from the aqueous phase. In such cases, more polar materials such as nucleic acids, proteins, buffers, and stabilizers will be left in the aqueous phase. Thereafter, the detectable moiety can be evaporated from the organic liquid phase, either in bulk (as in head space chromatography) or by a controlled heating pattern. Once the detectable moiety is in the gaseous phase it may be, but is not necessarily, detected in that phase. Thus it is contemplated that after transferring to a gaseous phase, materials including the detectable moiety may be recaptured on or in a solid or liquid phase, and especially in a chromatography column. Furthermore, it is contemplated that the entire gaseous phase including detectable moieties may be subjected to selective adsorption, absorption, condensation or the like, such as in a gas chromatography apparatus or an ion mobility apparatus, so as to separate the particular detectable moiety sought from other materials which migrate at different rates through the system. Exemplary ion mobility apparatus is described in U.S. Pat. Nos. 4,311,669 of Spangler et al., 4,390,784 of Browning et al., and 4,378,499 of Spangler et al. In such cases, the ultimate detection (by, for example, charge measurement, absorption, emission, photoionization or the like) need not itself be selective because of the selectivity provided by the selective absorption, ion mobility, adsorption or the like. Several such combinations of transferring to the gaseous phase, separation by a form of chromatography and detection by a form of emission or absorption are illustrated in the actual examples below (written in the past tense) and the predictive examples below (written in the present tense). The feasiblity of the predictive examples are demonstrated by the partial examples immediately preceding or following (which partial examples are written in the past tense).

Figure 2:
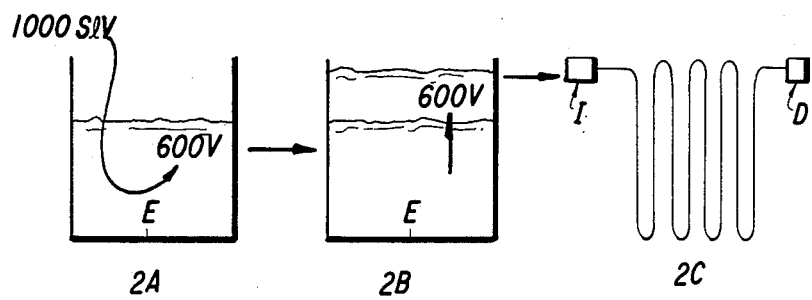
FIG. 2 illustrates the read-out part of the invention.

FIG. 2 illustrates schematically the read-out part of the present invention. An amount of enzyme (E) is in a tube after the specific binding reaction (as in FIGS. 1A, 1C-1J) or its activity is modulated (as in FIGS. 1B or 1K). A conjugate of sugar (S) linked to volatile moiety (V) by linkage (1) is introduced in a quantity stated as 1000 units. If, at the completion of a fixed period, enzymatic reaction has cleaved 600 units, 600 cleaved volatile moieties (V) will be in the aqueous phase. By then extracting with an organic phase, all or a fixed portion of such moieties are extracted into the organic phase (illustrated schematically in FIG. 2B). By then injecting an aliquot of the organic phase into the inlet (I) of a gas chromatograph, the volatile moieties (V) will migrate together and reach detector (D), causing a peak in the output of detector(D). Such output represents an amplified value positively correlated to the enzyme activity in the tube in FIG. 2A after the specific binding reaction. This output is therefore functionally related to target binding member concentration in the sample analyzed.

It should be appreciated from the above discussion that the concentration of the detectable moiety can occur before, during and/or after transfer to the gas phase. Thus, when extraction is conducted, the extraction step highly concentrates the detectable moiety relative to other components of the first (aqueous) phase. When chromatography or ion mobility separation is used, such concentration is performed in the gaseous phase or by interaction between the gaseous phase and a solid (or liquid) phase. By reciting a separate concentration step, however, it is intended to exclude analyses of the bulk vapor phase directly above the first phase, as in the measurement of carbon-14 labeled carbon dioxide after an enzyme immunoassay employing a decarboxylase in H. A. Fields et al., J. of Immunological Methods, vol. 47, pp. 145-59 (1981). Such direct measurement of radioactive gases liberated by the enzyme in Fields et al. has all of the disadvantages of radioactive immunoassays.

Suitable detection means beyond those mentioned above include those described in Chapter 5 "Detectors" at pages 213-280 of R. L. Grob, Modern Practice of Gas Chromatography (N.Y. 1977). In the discussion that follows, several illustrative gas phase detection methods are described. In each case, representative detectable moieties are illustrated. In the table that follows, illustrative precursors which are conjugates are shown containing such detectable moieties linked into a nonvolatile conjugate by an enzymatically cleavable linking moiety. At the end of such table classes of enzymes are listed, illustrative of the enzymes usable as tags in the various geometries of the present method. It should be appreciated that each enzyme has various counterparts known to the art which could also be used to cleave such enzymatically cleavable linkages. Similarly, for any enzyme, it should be readily apparent that numerous other conjugates could be used yielding the same or similar detectable moiety transferable to the gaseous phase.

The precursor need not, however, be such a conjugate cleavable to form the detectable moiety. Other types of precursors can be illustrated by the multistep chemical reaction utilized by K. Kobayashi et al., J. of Chromatography, Vol. 245, pp. 339-345 (1982) for determination of hydrogen peroxide (suggested as part of assays for oxidative enzyme activity):

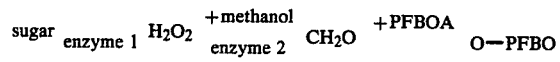

where the sugar can be glucose, enzyme 1 would then be the oxidative enzyme glucose oxidase, enzyme 2 could be catalase, PFBOA is pentafluorobenzyloxylamine and O-PFBO is O-pentafluorobenzyl oxime. If applied to the present invention, either enzyme 1 (e.g., glucose oxidase) or enzyme 2 (e.g., catalase) could be the tags on an antigen, antibody, nucleic acid or other binding pair member. At the conclusion of the assay, if the tag is glucose oxidase, read-out reagents including glucose, oxygen, methanol and catalase (all in excess relative to glucose oxidase tag) would be added. After the controlled period, PFBOA and O-PFBO would be extracted and injected into a gas chromatography equipped with an electron capture detector, or the entire aqueous solution would be injected. Separate signals for PFBOA and O-PFBO would be measured with a high degree of sensitivity. Similarly, if catalase were the tag, hydrogen peroxide, methanol and PFBOA would be added in excess for a controlled period. Injection, or extraction plus injection, would follow. Many other similar single or multistep reactions, moderated by an enzyme or other catalyst or co-catalyst used as the tag, could also be practised to convert the precursor to a volatile detectable moiety. It should be noted, however, that the precursor (methanol and PFBOA in the exemplary case) need not be non-volatile provided that the concentration and/or separation steps are sufficient to distinguish precursor from the desired detectable moiety.

The diagnostic assay kit of the present invention includes at least two reagents and two means for practicing the present method. One reagent contains the moderating moiety (e.g., enzyme) coupled to a binding pair member (other than the target binding pair member) capable of participating in the specific binding reaction. It should be apparent from FIGS. 1A-1K that such enzymatic conjugate can contain either an antigen, an antibody, a hapten, or a polynucleotide (either a probe polynucleotide or a labeled polynucleotide). The second reagent needed in the kit is the precursor or set of precursors (e.g., the conjugate containing a volatile detectable moiety linked into a nonvolatile conjugate by an enzymatically cleavable linking agent). Illustrative combinations of such enzyme conjugate and enzymatic reactant conjugate are illustrated below:

|     | Enzyme Tag | Cleavable Conjugate |
| --- | --- | --- |
| (1) | β-galactosidase | o-nitrophenyl-β-D-galactopyranoside |
| (2) | alkaline phosphatase | p-nitrophenylphosphate |
| (3) | acid phosphatase | p-nitrophenylphosphate |
| (4) | esterase | ethyl butyrate |
| (5) | urease | urea |

-continued

| Enzyme Tag | Cleavable Conjugate |
|---|---|
| (6) glutamate decarboxylase | L-glutamic acid |
| (7) arginine deaminase | L-arginine |

In similar fashion, appropriate conjugants and enzymes could be used, whereby the following volatile detectable moieties could be formed, transferred, concentrated and detected. In each case, the type of cleavable linkages that may be possible are indicated.

| Detectable Moiety | Structure | Linkage(s) |
|---|---|---|
| 1. Pentafluorobenzyl alcohol | $C_6F_5CH_2OH$ | ester, acetal |
| Pentafluorobenzoic acid | $C_6F_5COOH$ | ester |
| 2. Heptafluoro-1-butanol | $CF_3CF_2CF_2CH_2OH$ | ester, acetal |
| Heptafluorobutyric acid | $CF_2CF_2CH_2COOH$ | ester |
| 3. Pentafluoro-1-propanol | $CF_3CF_2CH_2OH$ | ester, acetal |
| Pentafluoropropionic acid | $CF_3CF_2COOH$ | ester |

Other similar detectable moieties may be used, especially containing halogen (e.g., chlorine or fluorine) or nitro, provided that the substitutions do not cause the cleaved detectable moiety to be excessively non-volatile (difficult to transfer to a gas phase in the particular overall system employed). Thus, certain highly chlorinated moieties may be too non-volatile. Additionally, the detectable moiety and overall conjugate should be selected as not undergoing side-reactions or spontaneous cleavage in the aqueous medium used for the selective binding reaction or the moderated chemical reaction.

Other suitable enzyme/cleavable conjugate combinations useful in the present invention include those known for pure assays for enzyme in a sample such as that described in B. Koppen et al., Anal. Biochem. Vol. 136, 272–275 (1984). Such enzymes can be grouped into several major categories, including hydrolases and lyases. Hydrolases include especially enzymes for cleaving an ester, amide or acetal linkage of a general or specific moiety linked to the detectable moiety (e.g., a specific sugar such as glucose or galactose). Lyases include enzymes which remove groups from their substrates, not by hydrolysis, leaving moieties with double bounds (as in decarboxylases producing carbon dioxide).

Suitable precursors other than such conjugates include those discussed above in relation to the Kobayashi et al. article.

EXAMPLE 1

Assay for Biotin

The immunoassay for biotin, performed by competitively reacting biotin and enzyme labelled biotin with avidin immobilized on a solid support, is described below.

Preparation of avidin coated polystyrene test tubes (as described by Parsons, G. H., Jr. in "Methods in Enzymology" (Langone, J. J. and Von Vunakis, H., Ed.) 1981, vol. 13, Part B, 224–239, Academic Press, New York). Avidin (5 mg) and bovine-γ-globulin (5 mg) were dissolved in 50 mL of 0.05M phosphate buffered saline (PBS) (pH 7.2). To this mixture, 0.1 mL of 25% aqueous glutaraldehyde was added. The resulting solution was incubated at 25° C. for 60 minutes then diluted 10 times with PBS. A 0.4 mL aliquot of this solution was dispensed into each polystyrene tube. The tubes were incubated at 37° C. for 2 hours, and then washed with water (3 times).

Preparation of biotinated-β-galactosidase

Biotinated-β-galactosidase was purchased from the Sigma Chemical Co. and used as received.

Competitive binding reaction: assay for biotin

A phosphate buffered saline solution of biotinated-β-galactosidase ($1.0 \times 10^{-8}$M in biotin) containing 0.05% Tween 20 was mixed with an equal volume of various biotin solutions ranging in concentration from $1 \times 10^{-6}$ to $1 \times 10^{-10}$M. A 0.5 mL aliquot of each of the resulting solutions was dispensed into the avidin coated polystyrene test tubes. The competitive binding reaction was carried out by incubating the tubes at 37° C. for 1.5 hours. The solutions were then discarded and the test tube washed 3 times with water. Subsequently, the quantity of immobilized enzyme was measured via hydrolysis of o-nitrophenyl-β-D-galactopyranoside. Each polystyrene tube was charged with 1.0 mL of 0.1M sodium phoshate buffer (pH 7.3), 0.05 mL of 3.36M β-mercaptoethanol and 0.05 mL of 0.03M magnesium chloride. The tubes were incubated at 37° C. for 5 minutes to activate the enzyme, followed by the addition of 0.1 mL of 0.068M o-nitrobenzyl-β-D-galactopyranoside. The hydrolysis of the substrate proceeded for 1 ½ hours at 37° C. Then 1 mL of diethyl ether containing 0.12 mg of nitrobenzene (internal standard) was added and the test tube vigorously shaken for 1 minute. Quantification of o-nitrophenol was effected via gas chromatographic analysis of the ethereal layer utilizing a 6 ft. glass column packed with 1% SP-1240 DA on 100/120 Supelcoport (Supelco Inc.'s trademark) equipped with a flame ionization detector supplied by Hewlett-Packard. The results are tabulated below.

TABLE 1

| ASSAY FOR BIOTIN | | |
|---|---|---|
| [Biotin] (moles/L) | $-\log$[Biotin] | o-Nitrophenol via GC (μ-moles) |
| $100 \times 10^{-8}$ | 6.0 | 0.132 |
| 50 | 6.3 | 0.126 |
| 25 | 6.6 | 0.186 |
| 10 | 7.0 | 0.233 |
| 5 | 7.3 | 0.304 |
| 4 | 7.4 | 0.335 |
| 2.5 | 7.6 | 0.529 |
| 1.0 | 8.0 | 0.697 |
| 0.5 | 8.3 | 0.896 |
| 0.25 | 8.6 | 1.069 |
| 0.10 | 9.0 | 1.171 |
| 0.05 | 9.3 | 1.221 |

EXAMPLE 2

Assay for Biotin

An immunoassay for biotin was carried out in a manner similar to that described in Example 1 except that the concentration of the avidin used to coat the polystyrene test tubes was reduced to 2 mg per 500 mL of buffer and the biotinated-β-galactosidase solution used in the competitive binding reaction was diluted by a factor of 2 (to $5.0 \times 10^{-9}$M in biotin and 0.25 units/mL in β-galactosidase). The results are tabulated below.

TABLE 2

ASSAY FOR BIOTIN

| [Biotin] (moles/L) | −log[Biotin] | o-Nitrophenol via GC (μ-moles) |
|---|---|---|
| 50 × 10⁻⁸ | 6.30 | 0.113 |
| 25 | 6.60 | 0.130 |
| 5 | 7.30 | 0.173 |
| 3 | 7.52 | 0.190 |
| 1.5 | 7.83 | 0.315 |
| 0.5 | 8.30 | 0.510 |
| 0.3 | 8.52 | 0.588 |
| 0.15 | 8.83 | 0.628 |
| 0.05 | 9.30 | 0.589 |
| 0 | — | 0.603 |

EXAMPLE 3

Assay for Biotin

An immunoassay for biotin was carried out in a manner similar to that described in Example 1 except that the concentration of biotinated-β-galactosidase was increased by a factor of 1.5 (to $1.5 \times 10^{-8}$M in biotin and 0.75 units/mL in β-galactosidase). The results are tabulated in Table 3.

TABLE 3

ASSAY FOR BIOTIN

| Biotin (moles/L) | −log[Biotin] | o-Nitrophenol via GC (μ-moles) |
|---|---|---|
| 50 × 10⁻⁸ | 6.30 | .460 |
| 5 | 7.30 | .544 |
| 4 | 7.40 | .538 |
| 3 | 7.52 | .587 |
| 2 | 7.70 | .758 |
| 1 | 8.00 | .964 |
| 0 | — | 1.180 |

EXAMPLE 4

Assay for Thyroxine

The immunoassay for thyroxine, performed by preparing a thyroxine-β-galactosidase conjugate and competitively reacting this conjugate and free thyroxine with immobilized antiserum raised against thyroxine, is described below.

Preparation of thyroxine methyl ester (according to the procedure described by Ashley, J. N. and Harrington, C. R., *Biochem. J.*, 1929, 22 1436–1445). A slurry was prepared containing 2.0 g (2.6 mmol) of thyroxine suspended in 25 mL of dry methanol. Upon saturation with a vigorous stream of anhydrous hydrochloric acid, the material dissolved and heat evolved. As the solution cooled, a white precipitate formed. After repeating the saturation with hydrochloric acid, the slurry was concentrated and the precipitate (thyroxine methyl ester hydrochloride) was collected by filtration and dried overnight in a vacuum desiccator. The ester hydrochloride was then dissolved in 200 mL of 50% aqueous methanol and neutralized with an equivalent of 2N sodium hydroxide. Some material precipitated; the yield may be increased by the addition of 100 mL of water and cooling in an ice bath. The crude product was collected on a frit, washed with water and dried under vacuum. Pure thyroxine methyl ester was afforded by recrystallizing the crude material from dilute aqueous methanol. ¹H NMR (CDCl₃) δ2.20 (2 H,s), 2.98 (2 H,d), 3.78 (1 H,m), 3.80 (3 H,s), 7.17 (2 H,s), 7.80 (2 H,s). Anal. Calcd for $C_{16}H_{13}I_4NO_4$: C, 24.3; H, 1.66; N, 1.77. Found: C, 24.0; H, 1.64; N, 1.63.

Preparation of m-maleimidobenzoyl thyroxine methyl ester (as described by Monji, N., Malkus, H, and Castro, A., *Biochem. Biophys. Res. Commun.*, 1978, 85, 671–677). m-Maleimidobenzoic acid (225 mg, 1.06 mmol) was dissolved in 4 mL of thionyl chloride and refluxed for 30 minutes. Removal of excess thionyl chloride under reduced pressure afforded m-maleimidobenzoyl chloride as a pale yellow solid. The acid chloride (220 mg dissolved in 10 mL of tetrahydrofuran) was added dropwise to a stirred suspension of 400 mg (0.51 mmol) of thyroxine methyl ester and 400 mg of sodium carbonate. After the addition was complete, the mixture was refluxed for 30 minutes. Removal of the solvent under reduced pressure yielded a crude yellow product. The material was purified by silica gel chromatography with chloroform as the eluent. ¹NMR (CDCl₃) δ 3.85 (3 H,s), 3.92 (1 H,m), 5.77 (1 H,s), 6.90 (2 H,s), 7.12 (2 H,s), 7.57 (2 H,m), 7.70 (2 H,s), 7.80 (2 H,m). Anal. calcd. for $C_{27}H_{18}I_4N_2O_7$: C, 32.8; H, 1.82; N, 2.80. Found: C, 32.7; H, 2.09; N, 2.42.

Preparation of thyroxine-β-galactosidase (as described by Monji, N., Malkus, H., and Castro, A., *Biochem. Biophys. Res. Commun.*, 1978, 85, 671–677). β-Galactosidase (2.5 mg), stored under an inert atomosphere and containing 18.5 moles of free sulfhydryl groups per mole (822 units per mg), was dissolved in 2.1 mL of degassed 0.05M phosphate buffered saline (pH 7.2). A 250 μl aliquot of tetrahydrofuran containing 0.2 mg/mL of m-maleimidobenzoyl thyroxine methyl ester was added and the resulting mixture incubated for 2 hours at 25° C. Following overnight dialysis in the same buffer, the material was chromatographed on a freshly prepared (30×1.5 cm) Sephadex G-25 column. A single fraction with enzymatic activity and a total volume of 10 mL was collected.

Purification of antiserum raised against thyroxine. A 0.75 mL aliquot of antiserum raised against thyroxine was diluted with 0.05M phosphate buffered saline (pH 7.2) to a final volume of 5 mL. A precipitate formed when this solution was combined with an equal volume of saturated ammonium sulfate. The mixture was centrifuged at 5000 rpm for 20 minutes while maintaining the temperature at 4° C. Subsequently, the supernatant liquid was discarded, and the pellet redissolved in 5 mL of the phosphate buffer.

Preparation of anti-thyroxine coated polystyrene test tubes (adapted from a procedure of Parson, G. H., Jr., in "Methods in Enzymology" (Langone, J. J. and Van Vunakis, H., ed.) 1981, vol. 13, Part B, 224–239, Academic Press, New York). A 0.2 mL aliquot of the purified antibody solution was diluted to 3 mL in 0.05M phosphate buffered saline (pH 7.2) which contained 0.05% glutaraldehyde. The solution was incubated for 1 hour at 25° C. and then diluted 60 times with the phosphate buffered saline. A 0.5 mL aliquot of this final solution was dispensed into each polystyrene test tube; the tubes were allowed to react at 37° C. for 2 hours. Subsequently, the solutions were discarded and the tubes washed 3 times with water.

Competitive binding reaction: assay for thyroxine. A solution of the thyroxine-β-galactosidase conjugate (approximately 4.0 unit/mL) dissolved in 0.05M phosphate buffered saline containing 0.05% Tween 20 was mixed with an equal volume of various thyroxine solutions (prepared in the same buffer) ranging in concentration from $1 \times 10^{-6}$ to $1 \times 10^{-10}$M. A 0.05 mL aliquot of each of the resulting solutions was dispensed into polystyrene test tubes coated with antisera raised against thyroxine. The competitive binding reaction was carried out by incubating the tubes at 37° C. for 2 hours at which time the solutions were discarded and the test tubes washed 3 times with water. The quantity of immobilized enzyme was measured via hydrolysis of o-nitrophenyl-$\beta$-D-galactopyranoside. Each polystyrene tube was charged with 1.0 mL of 0.1M sodium phosphate buffer (pH 7.2), 0.05 mL of 3.36M $\beta$-mercaptoethanol and 0.05 mL of 0.03M magnesium chloride. The tubes were incubated at 37° C. for 5 minutes to activate the enzymes followed by the addition of 0.1 mL of 0.068M o-nitrophenyl-$\beta$-D-galactopyranoside. The hydrolysis of the substrate proceeded at 37° C. for 2 hours. Then 1 mL of diethyl ether containing 0.12 mg of nitrobenzene (internal standard) was added and the test tube vigorously shaken for 1 minute. Quantification of o-nitrophenol was effected via gas chromatographic analysis of the ethereal layer utilizing a 6 ft glass column packed with 1% SP-1240 DA on 100/120 Supelcoport equipped with a flame ionization detector supplied by Hewlett-Packard. The results are tabulated in Table 4, last column. Corresponding analysis of the o-nitrophenol colorimetrically is tabulated in the third column of Table 4 for comparative purposes.

TABLE 4

ASSAY FOR THYROXINE

| [Thyroxine] (moles/L) | −log[Thyroxine] | o-Nitrophenol via Spectroscopy ($\mu$-moles) | o-Nitrophenol via GC ($\mu$-moles) |
|---|---|---|---|
| 42 × 10$^{-8}$ | 6.38 | 0.141 | 0.131 |
| 25 | 6.60 | 0.148 | 0.133 |
| 10 | 7.00 | 0.168 | 0.158 |
| 5.0 | 7.30 | 0.169 | 0.157 |
| 2.5 | 7.60 | 0.192 | 0.183 |
| 1.0 | 8.00 | 0.253 | 0.246 |
| 0.50 | 8.30 | 0.277 | 0.276 |
| 0.25 | 8.60 | 0.297 | 0.283 |
| 0.10 | 9.00 | 0.311 | 0.310 |
| 0.050 | 9.30 | 0.306 | 0.326 |
| 0.013 | 9.90 | 0.329 | 0.324 |
| 0 | — | 0.323 | 0.329 |

EXAMPLE 5

Assay of Thyroxine

An immunoassay for thyroxine was done in a manner similar to that described in Example 4 except that the thyroxine-$\beta$-galactosidase solution used in the competitive binding reaction was diluted by a factor of 4 (to 1.0 unit of enzyme per mL of that reagent or 0.5 units of enzyme per mL of reaction mixture). The results are tabulated below.

TABLE 5

ASSAY FOR THYROXINE

| [Thyroxine] (moles/L) | −log[Thyroxine] | o-Nitrophenol via GC ($\mu$-moles) |
|---|---|---|
| 42 × 10$^{-8}$ | 6.38 | 0.030 |
| 25 | 6.60 | 0.030 |
| 10 | 7.00 | 0.036 |
| 5 | 7.30 | 0.046 |
| 4 | 7.40 | 0.042 |
| 2.5 | 7.60 | 0.049 |
| 1.0 | 8.00 | 0.060 |
| 0.50 | 8.30 | 0.070 |
| 0.25 | 8.60 | 0.075 |
| 0.10 | 9.00 | 0.104 |
| 0.05 | 9.30 | 0.115 |

TABLE 5-continued

ASSAY FOR THYROXINE

| [Thyroxine] (moles/L) | −log[Thyroxine] | o-Nitrophenol via GC ($\mu$-moles) |
|---|---|---|
| 0 | — | 0.117 |

PARTIAL EXAMPLE 6

Ten samples containing o-nitrophenol were analyzed using an Ion Mobility Spectrometer (IMS) adapted for negative ion spectrum and operated at 50° C. Configurations similar to those shown in U.S. Pat. No. 4,378,499 to Spangler et al. (1983) (but without a membrane inlet and using an Ni-63 radioactive ionization source) were used. The IMS used for the experiments consisted of a 2 cm long reactor region and an 8 cm long drift region. Sample was introduced into the IMS by inserting a wire probe or syringe into a small hole provided in the inlet. The inlet was heated to 122° C. and was lined with TEFLON ® PTFE tubing to minimize sample holdup. After being desorbed from the wire probe or injected by the syringe, the sample was transported to the reactor by means of a purified air (<10 ppm H$_2$O) carrier gas which was drawn into the reactor by means of a suction pump on the exit of the cell. Purified air drift gas counterflowed through the drift region to eliminate excess sample from this critical region of the IMS cell. The IMS cell was heated to 53° C. A control was run for pure o-nitrophenol vapors (by exposing the tip of a steel probe to such vapors and then desorbing the vapors from the probe in the heated inlet of the IMS). The samples and response values are tabulated below:

|  | Response 1 (probe sampling of vapors) | Response 2 (probe sampling of liquid) | Response 3 (direct liquid injection) |
|---|---|---|---|
| o-nitrophenol in diethyl ether | | | |
| 1 × 10$^{-3}$ M | +++ | ++ | +++ |
| 1 × 10$^{-5}$ M | + | − | +++ |
| 1 × 10$^{-7}$ M | − | − | NM |
| 1 × 10$^{-9}$ M | − | − | + |
| o-nitrophenol in water | | | |
| 1 × 10$^{-3}$ M | ++ | ++ | ++ |
| 1 × 10$^{-5}$ M | − | − | + |
| 1 × 10$^{-7}$ M | − | − | − |
| 1 × 10$^{-9}$ M | − | − | − |
| o-nitrophenol and galactose in buffer with conjugate each being: | | | |
| 1 × 10$^{-3}$ M | ++ | | |
| 1 × 10$^{-5}$ M | + | Interference | |
| 1 × 10$^{-7}$ M | − | | |
| 1 × 10$^{-9}$ M | − | | |

+++ very strong,
++ strong,
+ weak,
− no peak attributable to o-nitrophenol observed.

Comparing the Response 1 curves (probe sampling of vapors over the liquids) for the three runs at 10$^{-3}$M, substantial response was observed in all cases, but the response from ethereal solution was about twice as great. For 10$^{-5}$M solutions, signals were observed, but they were much smaller than in the three cases at 10$^{-3}$M. Such probe sampling of the vapor over the three $10^{-7}$M and $10^{-9}$M solutions gave no appreciable response.

Comparing the Response 2 curves, the first solutions gave good response at $10^{-3}$M nitrophenol, but at $10^{-5}$M, the expected peak was not observed. The buffer solution performed unusually here in that the same 21 millisecond peak was observed at all four concentrations. Perhaps the conjugate o-nitrophenyl-b-D-galactopyranoide present in these solutions was carried by the probe with the aqueous buffer and decomposed thermally to generate o-nitrophenol which masked the limited amounts of o-nitrophenol in the four solutions.

Comparing the Response-3 curves of the solutions (aqueous and ether) injected directly into the IMS, only weak response under the special conditions of drying were observed at $10^{-3}$M in water. By contrast, excellent signals were observed at $10^{-3}$ and $10^{-5}$M and an easily detectable signal was observed even at $10^{-9}$M for the ethereal solutions. The $10^{-7}$M experiment is not reported (shown as "NM") because the diethyl ether evaporated before the data could be collected.

The above represent qualitative results are based upon limited experiments; but it is expected that the IMS could produce quantitative data from the reaction product solutions of the present invention with very high sensitivity and reliability.

EXAMPLE 7

The procedure of Example 4 is repeated through extraction with diethyl ether. Quantification of o-nitrophenol is effected via ion mobility detection as set forth in the final part (Response 3 values) of partial Example 6. Results are expected to be more sensitive by several orders of magnitude than in Example 4.

EXAMPLE 8

The procedure of Example 4 is repeated except that the gas chromatography column is equipped with an electron capture detector. The quantification of o-nitrophenol is expected to be more sensitive by several orders of magnitude compared to the data in Table 4.

What is claimed is:

1. A method for the determination of a target selective binding pair member in a biological fluid sample comprising the steps:
   (a) performing a specific reaction for the target selective binding pair member in the biological fluid sample to form a first liquid phase;
   (b) providing a reaction moderating enzymatic moiety bound to a binding pair member in the first liquid phase, the concentration or activity of the reaction moderating enzymatic moiety being a function of the amount of target selective binding pair member participating in the specific binding reaction;
   (c) providing in contact with the first phase, a precursor convertible by chemical reaction moderated by the reaction moderating enzymatic moiety into a detectable moiety in a volatile form;
   (d) transferring into a gaseous phase the detectable moiety formed from the precursor;
   (e) concentrating the detectable moiety relative to other components of the first phase; and
   (f) detecting the detectable moiety which has been concentrated and transferred into the gaseous phase.

2. The method of claim 1 wherein the target binding member is an antigen and the specific binding reaction is the binding of an antibody to the target binding member.

3. The method of claim 1 wherein the target binding member is a hapten and the specific binding reaction is the binding of an antibody to the target binding member.

4. The method of claim 1 wherein the target binding member is an antibody and the specific binding reaction is the binding of an antigen to the target binding member.

5. The method of claim 1 wherein the target binding member is a polynucleotide and the specific binding reaction is the binding of a complementary polynucleotide to the target binding member.

6. The method of claim 5 wherein the complementary polynucleotide is provided as a reagent complex of complementary polynucleotide bound to a labeled polynucleotide, and the labeled polynucleotide is displaced from the reagent complex by the binding of target selective binding pair member to complementary polynucleotide.

7. The method of claim 6 wherein the labeled polynucleotide is bound, directly or indirectly to the reaction moderating moiety.

8. The method of claim 7 wherein the reaction moderating moiety is an enzyme.

9. The method of claim 5 wherein the reaction moderating moiety is an enzyme.

10. The method of claim 1 wherein the reaction moderating moiety is an enzyme.

11. The method of claim 1 wherein the precursor is a substantially non-volatile conjugate containing a linkage cleavable by chemical reaction moderated by the reaction moderating moiety and containing the detectable moiety, with cleavage of the linkage releasing the detectable moiety in a volatile form.

12. The method of claim 11 wherein the linkage is selected from the group consisting of acetal, ester and amide linkages.

13. The method of claim 12 wherein the conjugate contains a sugar bound by the linkage to the detectable moiety.

14. The method of claim 13 wherein the sugar is monosaccharide.

15. The method of claim 14 wherein the monosaccharide is selected from the group consisting of glucose, galactose, fructose and mannose.

16. The method of claim 12 wherein the detectable moiety is a substituted phenyl with the linkage bound to a ring carbon and at least one other ring carbon has halo or nitro substituent.

17. The method of claim 11 wherein the detectable moiety contains a halo or nitro substituent.

18. The method of claim 1 wherein the transferring step (d) comprises extracting the detectable moiety from an aqueous liquid phase into an organic liquid phase and evaporating the detectable moiety from the organic liquid phase.

19. The method of claim 1 wherein the transferring step (d) comprises evaporating the detectable moiety from an aqueous liquid phase in which the conjugate has been cleaved.

20. The method of claim 1 wherein the detecting step (f) comprises subjecting the gaseous phase to electrons and determining electrons captured in the gaseous phase by the detectable moiety.

21. The method of claim 1 wherein the concentrating step (e) and detecting step (f) comprises ionizing the detectable moiety and determining the mobility of the detectable moiety in an electromagnetic field.

22. The method of claim 1 wherein the evaporating step (d), concentrating step (e) and detecting step (f) comprise entraining the detectable moiety in a gaseous stream of carrier gas and determining the migration of the detectable moiety through a gas chromatographic column.

23. The method of claim 22 wherein the detectable moiety migrated through the gas chromatographic column is determined by electron capture.

24. The method of claim 23 wherein the detectable moiety contains a nitro or halo substituent.

25. A diagnostic kit comprising:
 (a) a first reagent comprising an enzyme conjugated to a specific binding pair member capable of competing with the target binding pair member in a specific binding reaction,
 (b) a non-volatile conjugate containing a linkage clevable by chemical reaction catalyzed by the enzyme and containing a detectable moiety released in a volatile form from the conjugate upon cleavage of the linkage by the enzyme,
 (c) means for concentrating and transferring the detectable moiety to a gas phase, and
 (d) means for detecting detectable moiety which has been concentrated and transferred to the gas phase.

26. The diagnostic kit of claim 25 wherein the conjugate is a sugar bound by an acetal, ester is amide linkage to the detectable moiety.

27. The diagnostic kit of claim 26 wherein the sugar is a monosaccharide.

28. The diagnostic kit of claim 26 wherein the detectable moiety is a phenyl with the linkage bound to a ring carbon and at least one other ring carbon has a halo or nitro substitutent.

29. The diagnostic kit of claim 25 wherein the detectable moiety includes a halo or nitro substituent and the means for detecting is an electron capture detector.

30. The diagnostic kit of claim 25 wherein the means for separating comprises a gas chromatography column.

* * * * *